US008562595B2

(12) United States Patent
Plunkett et al.

(10) Patent No.: US 8,562,595 B2
(45) Date of Patent: Oct. 22, 2013

(54) RETINAL REGENERATION

(75) Inventors: Malcolm Plunkett, Crafers (AU); Aly Hussain, London (GB); John Marshall, Farnborough (GB)

(73) Assignee: Ellex R&D Pty Ltd, Adelaid, South Australia (AU)

( * ) Notice: Subject to any disclaimer, the term of this patent is extended or adjusted under 35 U.S.C. 154(b) by 1174 days.

(21) Appl. No.: 12/446,677

(22) PCT Filed: Oct. 25, 2007

(86) PCT No.: PCT/AU2007/001622
§ 371 (c)(1),
(2), (4) Date: Jun. 5, 2009

(87) PCT Pub. No.: WO2008/049164
PCT Pub. Date: May 2, 2008

(65) Prior Publication Data
US 2010/0049173 A1 Feb. 25, 2010

(30) Foreign Application Priority Data
Oct. 25, 2006 (AU) ................................. 2006905904

(51) Int. Cl.
*A61B 18/18* (2006.01)

(52) U.S. Cl.
USPC ........................................... 606/4; 424/78.04

(58) Field of Classification Search
USPC ........................ 606/4–6; 424/78.04
See application file for complete search history.

(56) References Cited

U.S. PATENT DOCUMENTS

| 5,066,293 | A | 11/1991 | Furumoto |
| 5,302,259 | A | 4/1994 | Birngruber |
| 5,549,596 | A * | 8/1996 | Latina ............................... 606/4 |
| 5,756,541 | A | 5/1998 | Strong et al. |
| 6,514,241 | B1 | 2/2003 | Hsia |
| 6,540,391 | B2 | 4/2003 | Lanzetta |
| 6,671,043 | B1 | 12/2003 | Huettman |
| 6,733,490 | B1 | 5/2004 | Falsini |

(Continued)

FOREIGN PATENT DOCUMENTS

| WO | 0191661 A1 | 12/2001 |
| WO | 02083041 A1 | 10/2002 |

(Continued)

OTHER PUBLICATIONS

Roider, J., "Spatial confinement of photocoagulation effects using high repetition rate laser pulses," Conference on Lasers and Electro-Optics, 1990, Anaheim, CA, vol. 7, pp. 168-169.

(Continued)

*Primary Examiner* — Victor Nguyen
(74) *Attorney, Agent, or Firm* — Fredrickson & Byron, PA

(57) ABSTRACT

A method of retinal regeneration which improves retinal function by reversal of the degradation of the transport properties of Bruch's membrane. The method involves irradiation through the cornea of the eye to the retinal pigmented epithelium by a laser pulse or sequence of laser pulses having a pulse duration in the range of 10 ps to 20 µs and at a wavelength in the range of about 500 nm to 900 nm. The method applies a radiant exposure which results in the damaging or altering of the retinal pigmented epithelium cells in such a manner as to trigger cellular responses which improve the hydraulic conductivity of Bruch's membrane without causing irreversible damage to adjacent retinal structures and layers.

23 Claims, 5 Drawing Sheets

(56) References Cited

U.S. PATENT DOCUMENTS

| | | |
|---|---|---|
| 7,115,120 B2 | 10/2006 | Lin |
| 2003/0179344 A1 | 9/2003 | Van DeVelde |
| 2004/0039378 A1 | 2/2004 | Lin |
| 2004/0133190 A1 | 7/2004 | Hobart |
| 2005/0027288 A1 | 2/2005 | Oyagi et al. |
| 2005/0048044 A1 | 3/2005 | Schwartz et al. |
| 2006/0111697 A1 | 5/2006 | Brinkmann et al. |
| 2007/0154465 A1* | 7/2007 | Kharazi et al. ............. 424/93.21 |

FOREIGN PATENT DOCUMENTS

| | | |
|---|---|---|
| WO | 03101325 A1 | 12/2003 |
| WO | 2004026099 A2 | 4/2004 |
| WO | 2004027487 A1 | 4/2004 |
| WO | 2006021040 A2 | 3/2006 |

OTHER PUBLICATIONS

Ahir, A. et al., "Expression of Metalloproteinases from Human Retinal Pigment Epithelial Cells and Their Effects on the Hydraulic Conductivity of Bruch's Membrane," Investigative Ophthalmology & Visual Science, Feb. 2002, vol. 43, No. 2, pp. 458-465.

Roider, J. et al., "Subthreshold (retinal pigment epithelium) photocoagulation in macular diseases: a pilot study," Br J Ophthalmol. Jan. 2000;84(1): pp. 40-47.

Guo, L. et al., "Age-Dependent Variation in Metalloproteinase Activity of Isolated Human Bruch's Membrane and Choroid," Investigative Ophthalmology & Visual Science, Oct. 1999, vol. 40, No. 11, pp. 2676-2682.

Moore, D. et al., "Age-Related Variation in the Hydraulic Conductivity of Bruch's Membrane," Investigative Ophthalmology & Visual Science, Jun. 2996, vol. 36, No. 7, pp. 1290-1297.

Starita, C. et al, "Localization of the Site of Major Resistance to Fluid Transport in Bruch's Membrane," Investigative Ophthalmology & Visual Science, Mar. 1997, vol. 38, No. 3, pp. 762-767.

Anderson, R. Rox et al., "Selective Photothermolysis: Precise Microsurgery by Selective Absoprtion of Pulsed Radiation," Science, Apr. 1983, vol. 220, pp. 524-527.

Starita, C. et al., "Decreasing hydraulic conductivity of Bruch's membrane, relevance to photoreceptor survival and lipofuscinoses," American Journal of Medical Genetics, 1995, 57(2): pp. 235-237.

Starita, C. et al., "Hydrodynamics of ageing Bruch's membrane: implications for macular disease," Experimental Eye Research, 1996, 62(5), pp. 565-571.

Marshall, J. et al., "Aging and Bruch's membrane," Marmor MF ed. The Retinal Pigment Epithelium: Function and Disease, New York, Oxford University Press, pp. 669-692.

Hussain, AA. et al., "Age-related alterations in the diffusional transport of amino acids across the human Bruch's-choroid complex," Journal of the Optical Society of America, A., Optics, Image Science, & Vision, 2002, 19(1), pp. 166-172.

Moorman, C. et al., "Clinical applications of the MicroPulse diode laser," Eye 13:145-150 (1999).

Roider, J. et al., "Subthreshold (retinal pigment epithelium) photocoagulation in macular diseases: a pilot study," J. Ophthamol. 84:40-47 (2000).

"PCT International Search Report dated Nov. 14, 2007 for PCT/AU2007/001622, from which the instant application is based," 3 pgs.

"PCT International Preliminary Report on Patentability dated May 26, 2008, from which the instant application is based," 5 pgs.

Roider, J. et al., "Response of the Retinal Pigment Epithelium to Selective Photocoagulation," Arch Ophthalmol—vol. 110, Dec. 1992, pp. 1786-1792.

Hussain, A.A. et al., "Transport Characteristics of Ageing Human Bruch's Membrane: Implications for Age-Related Macular Degeneration (AMD)," Chapter IV, Focus on Macular Degeneration Research, (Editor O.R. Ioseliani), ISBN 1-59033-898-7, Nova Science Publishers, Inc. NY (2004), pp. 59-103.

* cited by examiner

RETINAL REGENERATION

RELATED APPLICATIONS

This application claims priority to International Application No. PCT/AU2007/001622 filed Oct. 25, 2007, and to Australian Application No. 2005905904 filed Oct. 25, 2006, the teachings of which are incorporated herein by reference.

This invention relates to a method of improving the function of the retina of the human eye by improving the transport properties of Bruch's membrane. This invention may be beneficially used in the treatment of eye diseases, such as early Age-related Macular Degeneration (AMD) and Diabetic Macular Edema (DME) in which the function of Bruch's membrane has become impaired as part of a disease pathogenesis, or the treatment of degradation related to aging. The transport properties of Bruch's membrane are improved by a treatment which triggers Retinal Pigmented Epithelial (RPE) cell changes, including migration and division.

BACKGROUND TO THE INVENTION

The light sensing and signaling processes of the human retina require a high level of support in terms of energy supply and waste removal to ensure optimal functionality. A monolayer of epithelial cells, known as the retinal pigmented epithelium (RPE) separates the light sensing and signaling processes from the blood supply of the choroid and it controls many bi-directional support functions. The RPE cells are attached to a basement membrane, known as Bruch's membrane, which is a thin extra-cellular matrix of collagen layers which acts as a semi-permeable barrier between the RPE cells and blood vessels of the choroid. The work of Marshall, Hussain, et. al. over many years has shown that degradation of the transport functions of Bruch's membrane is a major contributor to loss or decline in visual function with normal aging or a more rapid decline due to diseases such as age-related macular degeneration (AMD) and is well described in the following references:

Starita C., Hussain A. A., Marshall J. (1995). Decreasing hydraulic conductivity of Bruch's membrane: relevance to photoreceptor survival and lipofuscinoses. American Journal of Medical Genetics. 57(2):235-7.

Moore D. J., Hussain A. A., Marshall J. (1995). Age-related variation in the hydraulic conductivity of Bruch's membrane. Investigative Ophthalmology & Visual Science. 36(7):1290-7.

Starita C., Hussain A. A., Pagliarini S., Marshall J. (1996) Hydrodynamics of ageing Bruch's membrane: implications for macular disease. Experimental Eye Research. 62(5):565-72.

Starita C., Hussain A. A., Patmore A., Marshall J. (1997) Localisation of the site of major resistance to fluid transport in Bruch's membrane. Invest. Opthalmol. Vis Sci. 38: 762-767.

Marshall J., Hussain A. A., Starita C., Moore D. J., Patmore A. L. (1998). Ageing and Bruch's membrane. In: Marmor M F ed. Retinal Pigment Epithelium: Function and disease. New York, Oxford University Press; pp. 669-692.

Hussain A A., Rowe L., Marshall J. (2002) Age-related alterations in the diffusional transport of amino acids across the human Bruch's-choroid complex. Journal of the Optical Society of America, A, Optics, Image Science, & Vision. 19(1): 166-72.

Hussain A A., Starita C., and Marshall J. (2004) Chapter IV. Transport characteristics of ageing human Bruch's membrane: Implications for AMD. In Focus on Macular Degeneration Research, (Editor O. R. Ioseliani). Pages 59-113. Nova Science Publishers, Inc. New York.

Guo L., Hussain A A., Limb G A., Marshall J (1999). Age-dependent variation in metalloproteinase activity of isolated human Bruch's membrane and choroid. Investigative Opthalmol. Vis Sci. 40(11): 2676-82.

Although these transport functions begin to degrade from birth, serious vision loss may not occur until later in life when the RPE/Bruch's membrane/choroid complex degrades to a point at which it can no longer sustain the neuro-retina, resulting in atrophy of the neuro-retina or stress induced responses such as choroidal new vessel (CNV) growth.

Although changes in diet and environment have been recommended to reduce the rate of age related loss of visual acuity, no direct treatment exists, and almost all current treatments for AMD are focused on treating late stage complications such as CNV's. Current treatments for CNV's include photo-dynamic therapy (PDT) (as described in U.S. Pat. No. 5,756,541 assigned to QLT phototherapeutics Inc) where a photosensitive drug is administered intravenously and then activated by a light source which is directed at the CNV, and intra-vitreal injections of drugs which inhibit the growth factors which promote new blood vessel growth (anti-VEGF).

In Diabetic Macular Edema (DME) fluid leakage from retinal blood vessels can pool within retinal spaces or between the RPE/photoreceptor interface. If the RPE is unable to remove this fluid due to compromised transport through Bruch's membrane vision loss can occur. Large clinical trials have shown that early laser treatment can reduce the risk of severe vision loss from DME, although the collateral damage caused by current laser treatment makes it unsuitable for treatment near the center of vision (fovea). Intra-vitreal anti-VEGF drugs have recently been used to stop or reduce the leakage however they do not improve the ability to remove existing fluid accumulation.

Lasers have been used for many years to treat retinal disorders, predominately using their ability to coagulate tissue. The degree of laser energy absorption in retinal layers and structures is highly dependant on the wavelength used and one of the major absorbing chromophores within the retina is the melanin which pigments the RPE cells. Although the current retinal lasers use wavelengths that are strongly absorbed by the melanin of the RPE cells, the duration of the laser pulses which are currently used allows time for thermal diffusion from the RPE cells to adjacent structures and is particularly damaging to the neuro-retina resulting in permanent loss of visual function at the treatment site.

Anderson and Parrish introduced the idea of Selective Photothermolysis in April 1983 in the journal Science, Vol 220 in which they taught that suitably brief pulses of selectively absorbed optical radiation can cause selective damage to pigmented structures, cells, and organelles in vivo. A laser device to perform selective photothermolysis was then described in U.S. Pat. No. 5,066,293 filed in March 1989 which included a method of treating vascular lesions. This concept of confining damage by the use of short laser pulses was then applied to retinal treatment by Roider and Birngruber in a paper titled "Spatial confinement of photo-coagulation effects using high repetition rate laser pulses" which was presented at the Conference on Lasers and Electro-Optics in May 1990 and then expanded on by Roider, Norman, Flotte, and Birngruber in a paper titled "Response of the Retinal Pigment Epithelium to Selective Photocoagulation", Archives of Ophthalmology, Vol 110, December 1992, accepted for publication April 1992 and presented at the annual meeting of the Association for Research in Vision and Ophthalmology in April 1991. In this latter paper an animal experiment was able to demonstrate selective damage to the RPE while largely sparing the overlying photoreceptors. This technique has become known as selective retinal therapy (SRT) and has since been applied to a number of late stage retinal diseases with the aim of producing a therapeutic benefit by forcing RPE cells to migrate and divide, but with limited success. The technique is well described by Lin in United States patent application 20040039378. Roider, Brinkmann, Wirbelauer, Laqua and Birngruber (Subthreshold photocoagulation in macular diseases: a pilot study, Br J. Opthalmol. 2000 January; 84(1):40-7) have carried out small clinical trials to demonstrate that short duration laser pulses can be used to contain the energy within the RPE cells and prevent neuro-retinal damage.

In United States patent application 20050048044, Schwartz describes the need to improve the function of Bruch's membrane, but the method described is similar to PDT in that a drug is administered that can be activated on the target membrane. Once activated the drug has a tissue degrading action on the membrane with the aim of improving it's transport properties.

OBJECT OF THE INVENTION

It is the object of this invention to provide a method of improving the function of the retina of the human eye by improving the transport properties of Bruch's membrane. Further objects will be evident from the following description.

DISCLOSURE OF THE INVENTION

In one form, although it need not be the only or indeed the broadest form, the invention resides in a method of retinal regeneration by irradiation through the cornea of the eye to the retinal pigmented epithelium by a laser pulse or sequence of laser pulses having a pulse duration in the range of 10 ps to 20 μs.

The laser pulse or pulses preferably have a wavelength in the range 500 nm to 900 nm. A wavelength of 532 nm is appropriate.

The radiant exposure of the laser pulses is sufficient to cause effect in the retinal pigmented epithelial.

In a further form the invention resides in a method of improving retinal function predominantly by partial reversal of the degradation of the transport properties of Bruch's membrane, comprising;
  selecting a retinal area for treatment which does not display signs of severe neuro-retinal or RPE damage or hemorrhage; and
  performing an intervention involving the application of electromagnetic radiation through the cornea to the back of the eye, wherein the radiation is applied as a pulse or pulses with a duration in the range of about 10 ps to 20 μs and at a wavelength in the range of about 520 nm to 900 nm, which will allow containment of absorbed energy within chromophores contained within the retinal pigmented epithelium; and wherein a radiant exposure is applied which results in the damaging or altering of the said retinal pigmented epithelium cells in such a manner as to trigger cellular responses which improve the hydraulic conductivity of Bruch's membrane without causing irreversible damage to adjacent retinal structures and layers.

The radiant exposure used during the procedure will preferentially be within the range 10 mJ/cm$^2$ to 400 mJ/cm$^2$ per pulse, which induces substantial retinal pigmented epithelium cell death with minimal retinal pigmented epithelium cell membrane rupture.

BRIEF DETAILS OF THE DRAWINGS

To assist in understanding the invention preferred embodiments will now be described with reference to the following figures in which.

DETAILED DESCRIPTION OF THE DRAWINGS

Figure 1:
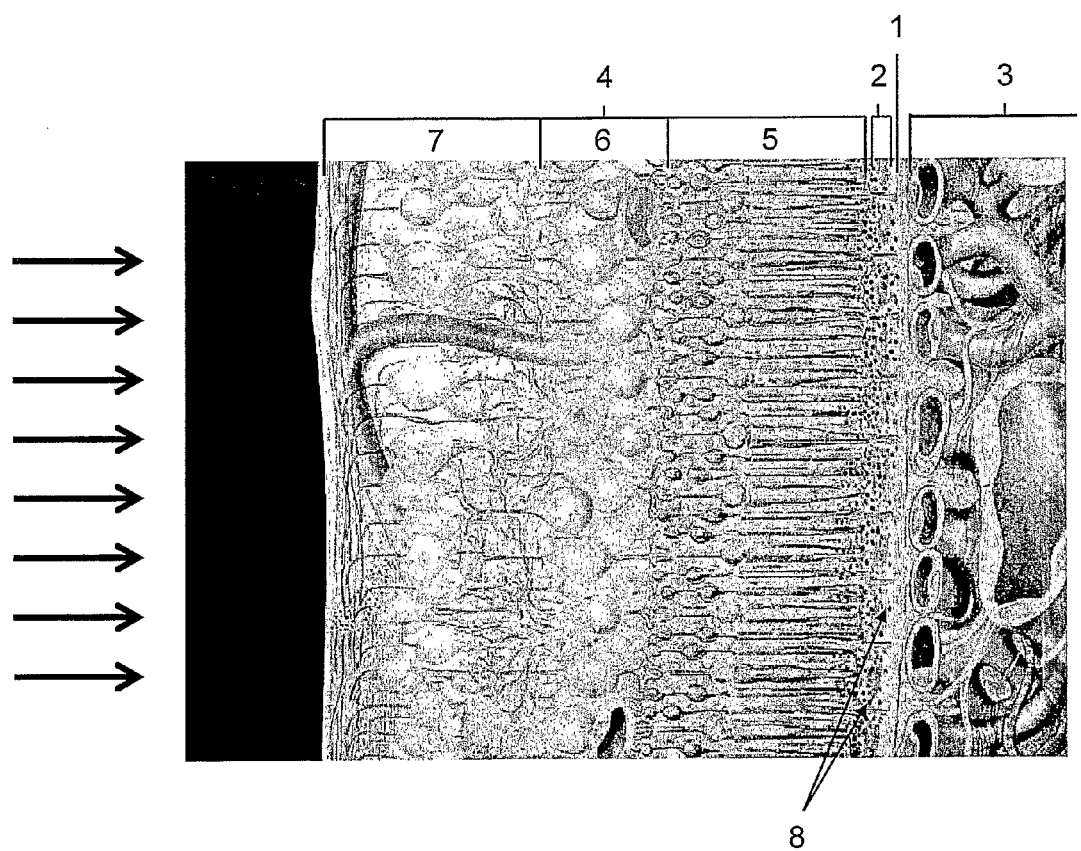
FIG. 1 is a cross-sectional diagram of a normal human retina.

An image of the human retina is shown in FIG. 1. Bruch's membrane 1 is located between the RPE 2 and the choroid 3. As described above, Bruch's membrane is a semi-permeable barrier between the blood supply delivered by the choroid and the RPE, which underlies the photosensitive neuro-retina 4. The neuro-retina 4 comprises photoreceptors 5, bipolar cells 6 and Ganglion cells 7.

Figure 2:
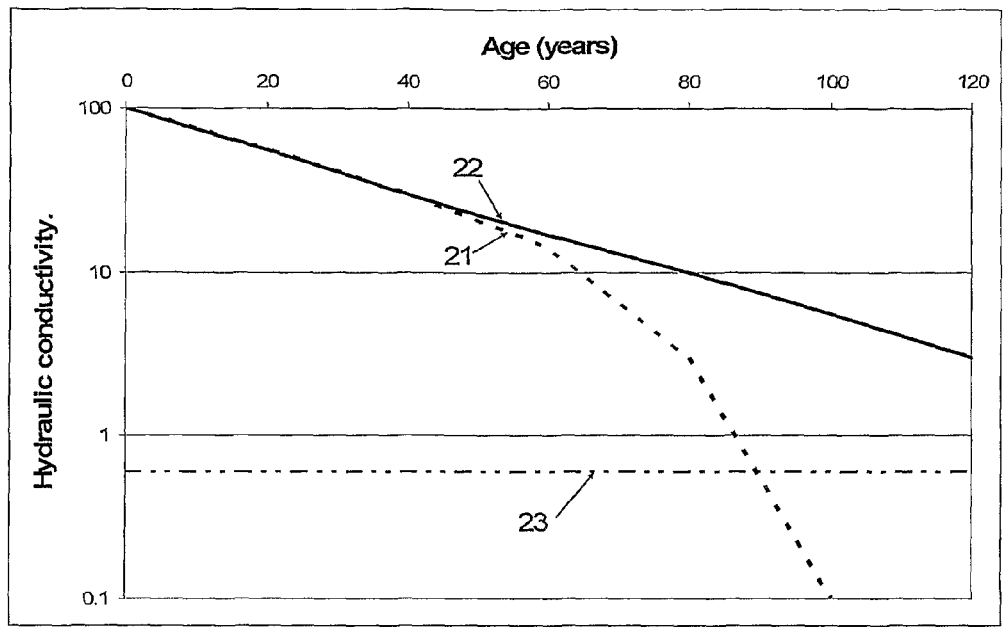
FIG. 2 is a graph which shows the typical degradation of Bruch's membrane transport due to aging and disease.

FIG. 2 shows a typical representation of the decline in the transport properties of Bruch's membrane. Accelerated degradation 21 compared to normal are-related degradation 22 can occur due to defective genes, environmental factors or disease which may lead to serious vision loss if the transport drops below a critical level 23 which is the minimum requirement for sustaining the neuro-retina. When this critical level is reached the overlying neuro-retina will begin to die in the macular region, resulting in a condition known as geographic atrophy, which will spread as the degradation continues, however as the transport is degraded down close to this point of system failure other complication can occur, such as CNV growth, which can further accelerate vision loss through blood leakage into the neuro-retina. Current treatments such as PDT or anti-VEGF drugs can be applied to slow or stop CNV growth and leakage however there is no current treatment available to alleviate the macular degeneration. Prior to any vision loss from geographic atrophy or CNV leakage other signs of degradation can be observed. One sign is the appearance of drusen between the RPE and neuro-retina, which is an accumulation of waste products, while another is an increase in the time required for the retina to adapt from light to dark conditions, which is caused by restricted energy supply to the photoreceptors. The level of a fluorescent waste product of the vision process, known as lipofuscin, within RPE cells can also provide a means of evaluating the degradation of the RPE/Bruch's membrane complex and can be viewed using fundus autofluorescence imaging. While it has been known for some time that these signs are precursors of the more serious and sight threatening problems of neuro-retinal atrophy and CNV growth, they are rarely used in clinical situations because no early intervention treatment exists.

Figure 3:
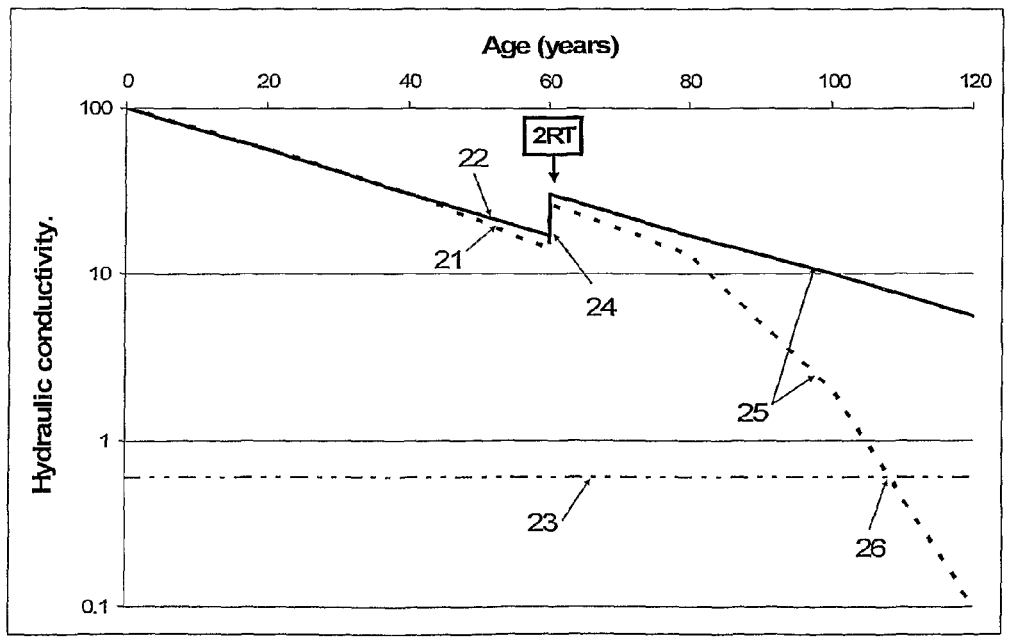
FIG. 3 is a graph which shows the effect of partial reversal of Bruch's membrane degradation of transport function.

FIG. 3 demonstrates the potential benefit of using the method of this invention to provide a partial reversal of the degradation of Bruch's membrane transport in delaying the decline and loss of visual function due to aging or disease. In this example Retinal Regeneration laser Therapy (2RT) has been applied at 60 years of age at point 24 which has achieved a partial reversal of Bruch's membrane degradation resulting in a delayed decline from aging or disease at point 25. Note that the rate of degradation from disease 21 is unchanged but the age at which line 21 crosses the critical level 23, where serious vision loss may occur, has now been considerably increased 26. It is an important feature of this method that the treatment is intended to be applied to areas of the retina which have suffered degradation but are still functional.

Figure 4:
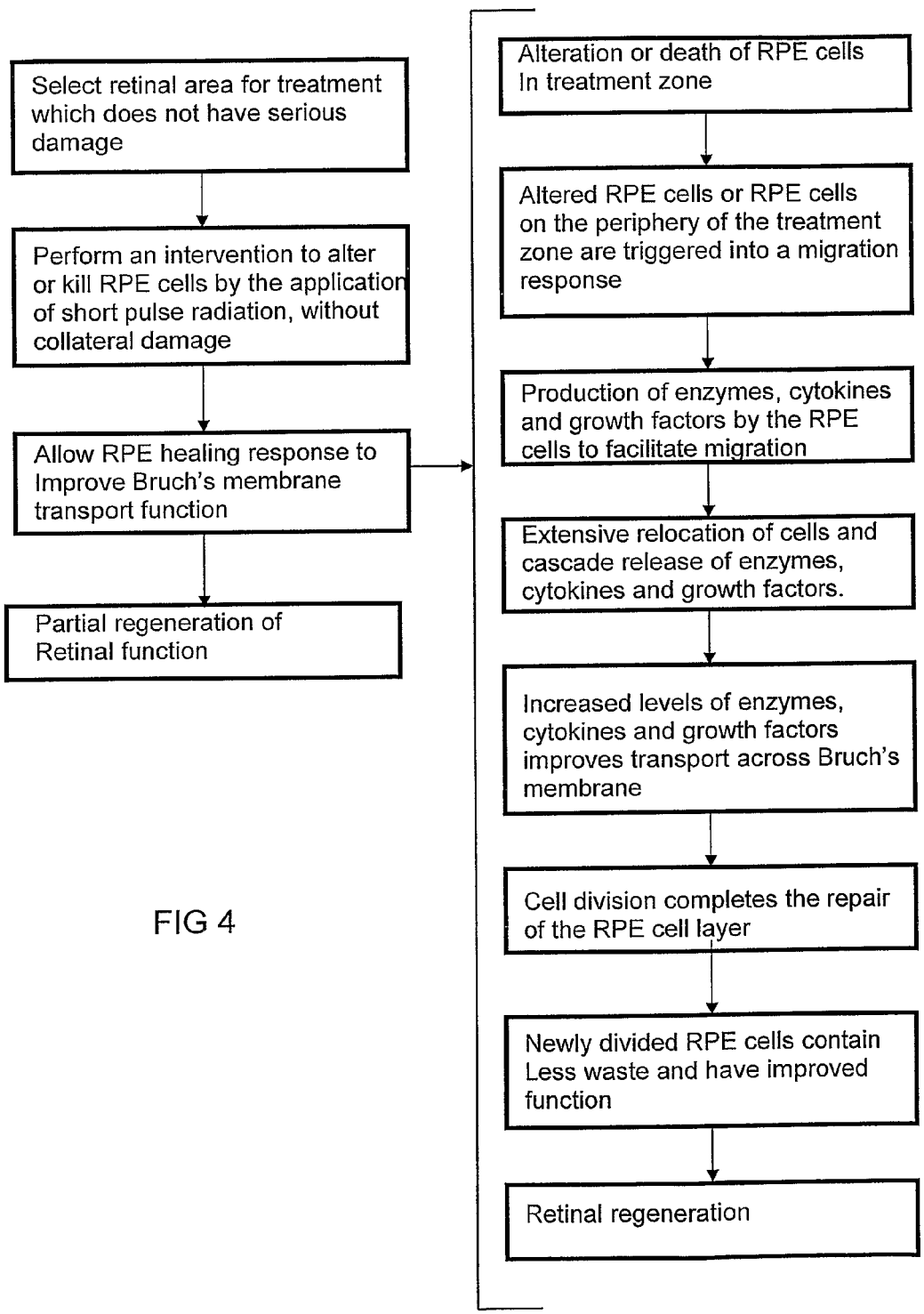
FIG. 4 is a sequential flow diagram showing the basic steps involved in the process of retinal regeneration and a detailed breakdown of the healing responses following treatment.

FIG. 4 is a sequential flow diagram which describes the method of retinal regeneration and a detailed breakdown of the healing responses following treatment. The initial assessment of impaired Bruch's membrane function can be performed using the indicators mentioned previously but it is intended that the method of retinal regeneration therapy is preferably performed before geographic atrophy or CNV growth occurs. The central area of the retina, known as the macular, has the greatest density of photoreceptors and correspondingly the highest demand on the RPE/Bruch's membrane/choriocappilaris complex and the highest rate of degradation, so for this reason the general macular region is primary target for regeneration. Because the improvement in Bruch's membrane transport extends beyond the irradiated area a pattern of separated treatment spots may be applied to treat a broad macular area. Areas in which the neuro-retina and RPE have already died from geographic atrophy or CNV's have developed or any areas of structural damage would not be selected for treatment.

RPE cells are pigmented with melanin contained within organelles known as melanosomes 8 (see FIG. 1) which perform the function of absorbing light which has passed through the neuro-retina in order to prevent back reflected light from degrading vision. Melanin absorbs light over a wide wavelength range however for treatment purposes the wavelength range from about 500 nm to 900 nm is preferred. The blue end of the spectrum is usually avoided due to it's photo-toxicity and at wavelengths beyond the infra-red end of the spectrum the amount of absorption reduces which allows a greater amount of radiation to pass though the RPE and into the choroid.

Laser radiation is preferably used to deliver specific wavelengths and a wavelength of 532 nm would be useful to perform the method of this invention, which can be obtained by frequency doubling the 1064 nm laser radiation from an Nd:YAG laser cavity.

Figure 5:
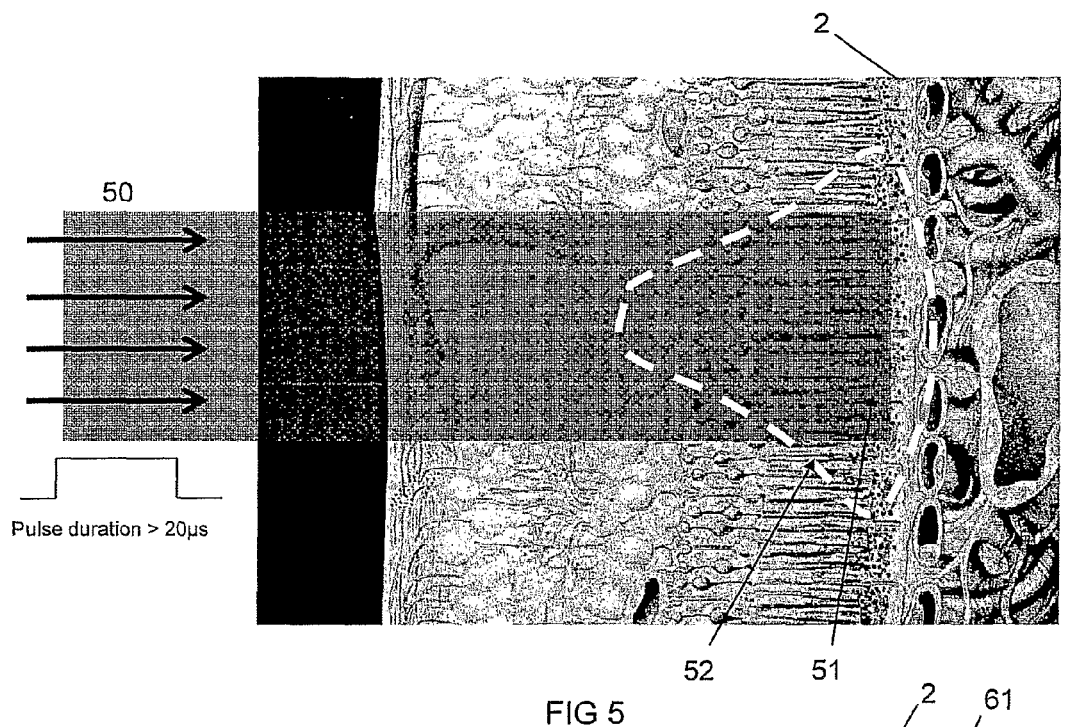
FIG. 5 is a cross-sectional diagram of a human retina showing neuro-retinal damage from thermal diffusion.

A critical aspect of this method is the application of radiation which can kill or alter RPE cells but cause no irreversible damage to the neuro-retina or other retinal layers or structures. To achieve this it is necessary to contain the effects of the energy absorption by the melanosomes within the RPE cells. This is only possible if radiation energy is deposited into the melanosomes in less than about 20 μs, to prevent thermal diffusion beyond the RPE cell membrane from occurring, however current retinal lasers typically use 10-200 ms pulse durations resulting in collateral damage as shown in FIG. 5, causing irreversible damage to the neuro-retina. In FIG. 5 the laser beam 50 impinges on the RPE 2 and energy is absorbed in the irradiated zone 51. However, thermal damage extends to a wider zone 52.

Figure 6:
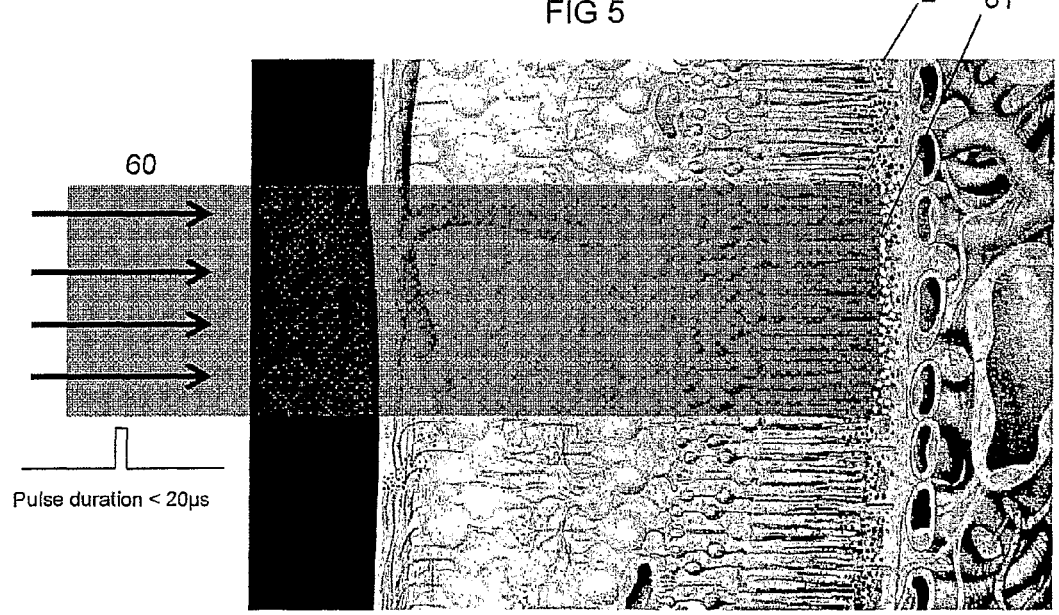
FIG. 6 is a cross-sectional diagram of a human retina showing thermal confinement within the RPE and FIG. 7 is a graph showing the measured hydraulic conductivity of Human donor Bruch's membrane.

FIG. 6 shows the effect of shorter laser pulse durations of <20 μs in which thermal effects are contained within the RPE cells, allowing them to be altered or killed without damage to the photoreceptors or other layers or structures. Pulse durations less than 10 ps are unlikely to be useful due to mechanically disruptive effects caused by stress confinement within the beam path. Pulse durations in the range 1 ns to 5 ns are readily achievable and most suitable. In FIG. 6 the laser beam 60 impinges on the RPE 2 and energy is absorbed to alter the RPE cells 61 without adjacent thermal damage.

A laser system capable of this type of treatment has been described in our co-pending patent application WO2006021040 however other devices which meet the described criteria could also be used. In particular it would be possible to use a flashlamp pumped, passively Q-switched Nd:YAG laser cavity which is extra-cavity frequency doubled to produce 532 nm pulses of approximately 3 ns in duration, similar to that described in our co-pending patent application WO2004027487. At this pulse duration energy absorption by the melanosomes in granules within the RPE cells can readily produce micro-bubbles which can be effective in killing or altering the RPE cells.

In laboratory experimentation it has been established that RPE cells can be killed by intra-cellular micro-bubbles over a wide energy range without rupturing cell membranes. In human explant samples in-vitro this range was found to be from approximately 35 to 160 mJ/$cm^2$ when using 3 ns pulses and a wavelength of 532 nm. Typically a sequence of three pulses is found to be appropriate although a single pulse or possibly 5 or more pulses may also be suitable. A sequence of up to 5 pulses may be required to ensure that all areas of the laser spot have received adequate irradiation, however a cumulative thermal effect on the melanosomes is not required or desirable so a low repetition rate is preferred.

The radiant exposure level required to kill or alter RPE cells, without rupturing the cell membranes, will produce no visible effect when these short pulse durations are used and in addition, the level of absorption will be dependant on the melanin content of the RPE cells which varies from patient to patient and with the region of the retina that is being treated. For these reasons it is useful to have a method of individual dose determination. This can be simply achieved by using visual effect scaling in which the exposure level required to produce a visual effect, such as bubbles or a lesion, can be determined by applying higher energy radiation in the periphery of the retina and then scaling down this level to an appropriate level for the regeneration therapy. This process is known as visible effect scaling. A typical radiant exposure which is at the threshold of producing a visible effect in the periphery of the retina may be 160 mJ/$cm^2$ which could be produced using an energy of 200 μJ and a 400 μm treatment spot. The energy may then be scaled back to one third of that value, for example, and an energy setting of 67 μJ used to deliver a radiant exposure of 53 mJ/$cm^2$ for performing the retinal regeneration therapy.

Laboratory experimentation has shown that when 3 ns pulses are used the first visible effect is from the formation of a macro-bubble, which results from intra-cellular micro-bubbles bursting the RPE cell membranes and coalescing into a visible macro-bubble. At this threshold level only minor non-permanent damage occurs to photoreceptors making it an ideal energy level marker to enable individual dose determination. Radiant exposure levels well above the visible effect threshold are to be avoided to reduce the risk of damaging photoreceptors. The optimum dose will use radiant exposure levels which are able to internally damage the RPE cells and trigger acute, or chronic, cell death without rupturing the cell membrane. Typically this may require a radiant exposure of 10 mJ/cm² to 400 mJ/cm² per pulse although a range of nominally 30 mJ/cm² to 250 mJ/cm². per pulse will generally be appropriate FIG. 4 also shows the sequence of cellular responses following the retinal regeneration treatment which result in improved Bruch's membrane transport and can be summarized as follows:

1. The alteration or death of RPE cells within the treated areas triggers altered or undamaged RPE cells on the periphery of the laser treatment zone to migrate, or initiate a migratory response, in order to restore the continuity of the RPE monolayer. However, before the cells can migrate they must degrade their attachment to Bruch's membrane and do so by increasing their production and expression of enzymes such as active matrix metalloproteinase (MMP), cytokines and growth factors. Laboratory experimentation has shown the up-regulation of active MMP-9 following laser insult and the paper by Ahir A., Guo L., Hussain A A., Marshall J. (2002) Expression of metalloproteinases from human retinal pigment epithelial cells and their effects on the hydraulic conductivity of Bruch's membrane, Investigative Ophthalmology and Visual Science, 43(2): 458-65 has shown MMP up-regulation during cell migration.
2. The migration of cells then results in an extensive relocation of cells in the surrounding areas and an accompanying cascade release of enzymes, cytokines and growth factors. This causes an improvement in the transport properties of Bruch's membrane in and around the treated area. The paper mentioned above in 1. also shows the improvement in the transport functions of Bruch's membrane following the application of active MMP's and the proliferation of Human RPE cells.
3. Cell division completes the healing process of the RPE cell layer, leaving no lasting damage to the target area or surrounding areas and the newly divided cells contain reduced waste products and are better able to perform their functions, such as fluid transport.

Figure 7:
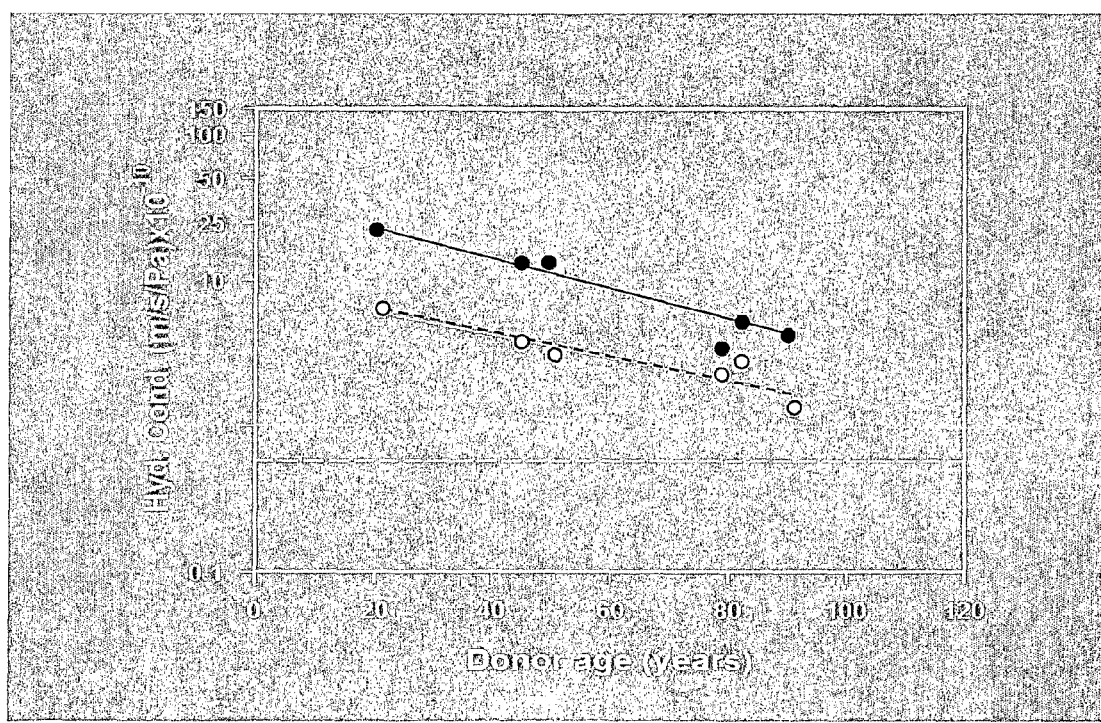

The measured hydraulic conductivity of Human donor Bruch's membrane is shown graphically in FIG. 7, which demonstrates that the theoretical improvement shown in FIG. 3 can be obtained by initiating the migration and division of RPE cells. The original hydraulic conductivities are shown as the dashed line and circles at the data points. After measuring conductivity, these samples of Bruch's membrane were plated with ARPE-19 cells and incubated for 24 hours. The RPE cells were then removed and conductivities re-assessed (solid line with dots at the data points). Proliferating ARPE-19 cells resulted in considerable improvement in the hydraulic transport properties of ageing human Bruch's membrane.

In the figure, the dashed horizontal line refers to the minimum hydraulic conductivity required to cope with fluid output from the RPE. These ARPE-19 experiments show that elevation of ageing curves is possible in order to avoid the early insults that can progress to macular disease.

This invention may be used to provide Retinal Regeneration Therapy (2RT), in order to treat early age-related macular degeneration, diabetic macular edema, or other diseases where the function of the neuro-retina is compromised due to impaired function of the RPE/Bruch's membrane/choriocapillaris complex. This procedure will be most effective in the earliest stages of these diseases before permanent damage has occurred to the neuro-retina or to delay retinal degradation through aging.

The invention claimed is:

1. A method of improving Bruch's membrane transport function by irradiation through the cornea of the eye to the retinal pigmented epithelium, the method comprising:

selecting an area of the retinal pigmented epithelium for treatment which does not display signs of severe neuro-retinal or retinal pigmented epithelium damage or hemorrhage; and irradiating the area with a laser pulse or sequence of laser pulses having a pulse duration in the range of 10 ps to 20 µs, thereby to damage or alter retinal pigmented epithelium cells in the area so as to trigger cellular responses which improve the hydraulic conductivity of Bruch's membrane without causing irreversible damage to adjacent retinal structures and layers.

2. The method of claim 1 wherein the laser pulse or sequence of laser pulses have a wavelength in the range 500 nm to 900 nm.

3. The method of claim 1 wherein the laser pulse or sequence of laser pulses have a wavelength of 532 nm.

4. The method of claim 1 wherein the laser pulse or sequence of laser pulses have a pulse duration of less than 20 µs and greater than 10 ps.

5. The method of claim 1 wherein the laser pulse or sequence of laser pulses have a pulse duration in the range 1 ns to 5 ns.

6. The method of claim 1 wherein the laser pulse or sequence of laser pulses have a pulse duration of 3 ns.

7. The method of claim 1 wherein a radiant exposure of the laser pulse or sequence of laser pulses is sufficient to cause effect in the retinal pigmented epithelial.

8. The method of claim 1 wherein a radiant exposure is within a range which induces substantial retinal pigmented epithelium cell death with minimal retinal pigmented epithelium cell membrane rupture.

9. The method of claim 1 wherein a radiant exposure of the laser pulses is determined by visual effect scaling.

10. The method of claim 1 wherein a radiant exposure of the laser pulses is in the range 10 mJ/cm² to 400 mJ/cm² per pulse.

11. The method of claim 1 wherein a radiant exposure of the laser pulses is nominally 30 mJ/cm² to 250 mJ/cm² per pulse.

12. The method of claim 1 comprising a sequence of up to five laser pulses.

13. The method of claim 1 comprising a sequence of three laser pulses.

14. A method of improving Bruch's membrane transport function by irradiation, the method comprising; selecting an area of the retinal pigmented epithelium for treatment which does not display signs of severe neuro-retinal or retinal pigmented epithelium damage or hemorrhage; and performing an intervention involving the application of electromagnetic radiation through the cornea to the back of the eye, wherein the radiation is applied as a pulse or sequence of pulses with a duration in the range of about 10 ps to 20 µs and at a wavelength in the range of about 500 nm to 900 nm, which allows containment of absorbed energy within chromophores contained within the retinal pigmented epithelium; and wherein a radiant exposure is applied which results in the damaging or altering of the retinal pigmented epithelium cells in such a manner as to trigger cellular responses which improve the hydraulic conductivity of Bruch's membrane without causing irreversible damage to adjacent retinal structures and layers.

15. The method of claim 14 wherein the laser pulse or sequence of laser pulses have a wavelength of 532 nm.

16. The method of claim 14 wherein the laser pulse or sequence of laser pulses have a pulse duration of less than 20 µs and greater than 10 ps.

17. The method of claim 14 wherein the laser pulse or sequence of laser pulses have a pulse duration in the range 1 ns to 5 ns.

18. The method of claim 14 wherein the laser pulse or sequence of laser pulses have a pulse duration of 3 ns.

19. The method of claim 14 wherein a radiant exposure of the laser pulses is determined by visual effect scaling.

20. The method of claim 14 wherein a radiant exposure of the laser pulses is in the range 10 mJ/cm$^2$ to 400 mJ/cm$^2$ per pulse.

21. The method of claim 14 wherein a radiant exposure of the laser pulses is nominally 30 mJ/cm$^2$ to 250 mJ/cm$^2$ per pulse.

22. The method of claim 14 comprising a sequence of up to five laser pulses.

23. The method of claim 14 comprising a sequence of three laser pulses.

* * * * *